US00PP37524P2

(12) United States Plant Patent
Nannes

(10) Patent No.: US PP37,524 P2
(45) Date of Patent: Jul. 14, 2026

(54) ***PEPEROMIA* PLANT NAMED 'BINL-77430004'**

(50) Latin Name: *Peperomia berteroana x inaequalifolia*
Varietal Denomination: BINL-77430004

(71) Applicant: Botanical Innovation B.V., Wageningen (NL)

(72) Inventor: Jacob A. M. Nannes, Nairobi (KE)

(73) Assignee: Botanical Innovation B.V.

( * ) Notice: Subject to any disclaimer, the term of this patent is extended or adjusted under 35 U.S.C. 154(b) by 0 days.

(21) Appl. No.: 19/377,230

(22) Filed: Nov. 3, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP33,033 P2 * 5/2021 Smit ..... Plt./373

* cited by examiner

*Primary Examiner* — Karen M Redden

(57) ABSTRACT

A new and distinct cultivar of *Peperomia* plant named 'BINL-77430004' is disclosed, characterized by glossy, bright green leaves. Plants have a distinct habit with a thick, upright stem with horizontally held leaves arranged in a sub-alternate pattern around the stem with very short internodes, giving the appearance a rosette from above. The new cultivar is a *Peperomia*, typically used as an ornamental plant.

1 Drawing Sheet

Latin name of the genus and species: *Peperomia berteroana x inaequalifolia.*

Cultivar denomination: 'BINL-77430004'.

BACKGROUND OF THE INVENTION

The new cultivar is a product of a planned breeding program by the inventor to develop new, distinctive, and better performing *Peperomia* cultivars. The seed parent is *Peperomia berteroana*, the species itself (unnamed and unpatented). The pollen parent is *Peperomia inaequalifolia*, the species itself (unnamed and unpatented). The crossing resulting in this new cultivar was made in May 2020 at a nursery in Nairobi, Kenya. 'BINL-77430004' was found and selected by the inventor in August 2021 at the same location.

Asexual reproduction of the new cultivar 'BINL-77430004' by leaf cuttings was first performed in at a commercial nursery in Nairobi, Kenya in August 2021, and has shown that the unique features of this cultivar are stable and reproduced true to type through successive generations.

SUMMARY OF THE INVENTION

The cultivar 'BINL-77430004' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77430004'. These characteristics in combination distinguish 'BINL-77430004' as a new and distinct *Peperomia* cultivar:

1. Glossy bright-green elongated leaves.

2. Distinct plant habit with a thick, upright stem with horizontally held leaves arranged in a sub- alternate pattern around the stem with very short internodes, giving the appearance a rosette from above.

PARENT COMPARISONS

Plants of the new cultivar 'BINL-77430004' are similar to plants of the seed parent in most horticultural characteristics, however, plants of the new cultivar 'BINL-77430004' differ in the following characteristics:

1. Leaves of the new cultivar are elongated with a more rounded tip, while leaves of the seed parent are elongated with a more pointed tip.
2. Leaves of the new cultivar are less reflexed downward than leaves of the seed parent.

Plants of the new cultivar 'BINL-77430004' are similar to plants of the pollen parent in most horticultural characteristics, however, plants of the new cultivar 'BINL-77430004' differ in the following characteristics:

1. Internodes of the new cultivar are shorter (about 50%-to 80% shorter) than internodes of the pollen parent.
2. Leaf color of the new cultivar is glossy bright green, while the leaf color of the pollen parent is slightly less glossy and slightly darker green.

COMMERCIAL COMPARISONS

Plants of the new cultivar 'BINL-77430004' are similar to plants of the commercial cultivar *Peperomia nivalis*, the species itself. However, plants of the new cultivar differ in the following characteristics:

1. Leaf color of the new cultivar is glossy bright green, while the leaf color of this comparator is dull green on the upper side.
2. Leaves of the new cultivar are about 30% larger than leaves of this comparator.
3. Attitude of leaves of the new cultivar is nearly horizontal, while leaves of this comparator are held strongly upwards, showing the silver-green underside Plants of the new cultivar 'BINL-77430004' are similar to plants of the commercial cultivar *Peperomia asperula*, the species itself. However, plants of the new cultivar differ in the following characteristics:

1. Leaves of the new cultivar are about 40% larger than leaves of this comparator.
2. Attitude of leaves of the new cultivar is nearly horizontal, while leaves of this comparator are held strongly upwards, showing the light green underside.
3. Young leaves of the new cultivar have a mainly flat aspect, while young leaves of this comparator are folded from the midvein.

BRIEF DESCRIPTION OF THE PHOTOGRAPH

The accompanying photograph illustrates in full color a top-down view of a typical plant of 'BINL-77430004' grown in a greenhouse. The plant is approximately 14 weeks of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2019 except where general terms of ordinary dictionary significance are used. The following observations and measurements describe 'BINL-77430004' plants at 14 weeks of age, grown in a greenhouse in August in Nairobi, Kenya. The growing temperature ranged from 18° C. to 20° C. at night to 20° C. to 28° C. during the day. Measurements and numerical values represent averages of typical flowering types.

Botanical classification: *Peperomia berteroana* x *inaequalifolia* 'BINL-77430004'.

PROPAGATION

Time to initiate roots: About 14 days at 20° C. in summer; 21 days at 20° C. in winter.

Time to produce rooted cutting: About 45 days at 20° C. in summer; 60 days at 20° C. in winter.

Description of roots: Fleshy, medium thickness, moderately dense, moderate branching. White in color, not accurately measured with R.H.S. chart.

PLANT

Plant type: Tender perennial potted plant.

Plant shape: Hemispherical.

Growth habit: Main stems grow from the base, no lateral branches present.

Plant spread: 7.3 cm.

Height: 5.3 cm.

Growth rate: Moderate.

Plant vigor: Moderate.

Age of plant described: Approximately 14 weeks.

Branching habit: Main stems grow from the base, no lateral branches present.

Pinching: Pinching not required.

Number of primary (main) branches per plant: Average 1 at this age.

Main branches:

*Length*.—Average: 3.2 cm.

*Diameter*.—Average: 7.5 mm.

*Internode length*.—Average: 4.5 mm.

Appearance and shape: Circular.

Luster: Glossy.

Aspect/angle from vertical: Average 17.5° from vertical.

Strength: Moderately strong.

Color:

*Developing*.—RHS Yellow-Green NN144C.

*Mature*.—RHS Yellow-Green 144A.

*At internodes*.—RHS Yellow-Green 144A.

Pubescence: None.

FOLIAGE

Leaf:

*Arrangement*.—Sub-alternate, single.

*Quantity*.—Average 12.

*Average length*.—4.2 cm.

*Average width*.—2.3 cm.

*Shape of blade*.—Obovate.

*Whole leaf dimension description*.—Carinate, succulent.

*Apex*.—Bluntly acute to rounded.

*Base*.—Attenuate.

*Margin*.—Entire.

*Aspect*.—Nearly flat.

*Attitude*.—Horizontal.

*Texture of top surface*.—Glabrous, smooth, moderately leathery.

*Texture of bottom surface*.—Glabrous, smooth, moderately leathery.

*Pubescence*.—None.

*Luster, upper side*.—Very glossy.

*Luster, under side*.—Matte.

*Rugosity*.—Both sides non-rugose.

*Color*.—Young foliage upper side: RHS Yellow-Green 144A. Young foliage under side: RHS Yellow-Green 144A and 144B. Mature foliage upper side: RHS Yellow-Green 147A flushed 139A, base 143A. Mature foliage under side: RHS Yellow-Green 144A, slightly darker towards the top.

*Venation*.—Pattern: Pinnate, with conspicuous main veins. Venation color upper side: RHS Yellow-Green 144A on lower half; no venation visible on upper half. Venation color under side: RHS Yellow-Green 144B.

*Petiole*.—Length: 1.3 cm. Diameter: Petiole slightly flattened, average diameter at widest (horizontal): 2.9 mm, average diameter at narrowest (vertical): 2.1 mm. Texture: Glabrous, smooth. Luster: Both sides matte. Strength: Medium. Color, upper side: RHS Yellow-Green 145A. Color, under side: RHS Yellow-Green 145A.

Other leaf characteristics: Leaves succulent, average thickness: 3.5 mm, upper 2.5 transparent.

FLOWER

Flowers not observed to date.

REPRODUCTIVE ORGANS

Not observed.

OTHER CHARACTERISTICS

Seeds and fruits: None observed to date.

Disease/pest resistance: Neither resistance nor susceptibility to normal diseases and pests of *Peperomia* observed.

Temperature tolerance: Tolerates temperatures from 10° C. to 40° C. Intolerant to wind and rain Hardy to USDA zones 11 to 13.

Tolerance to rain: Moderate to high.

Tolerance to wind: Moderate.

What is claimed is:

1. A new and distinct cultivar of *Peperomia* plant named 'BINL-77430004' as herein illustrated and described.

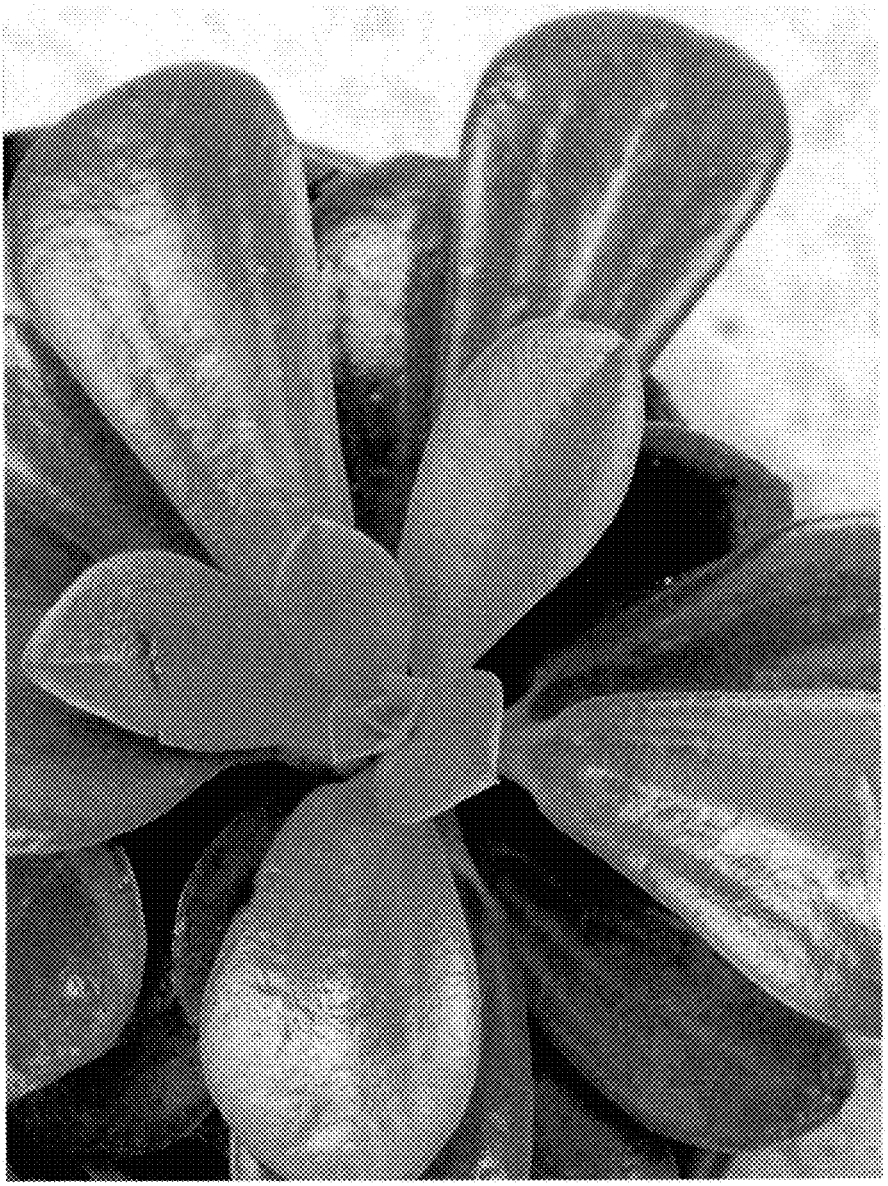

* * * * *